United States Patent [19]
VonBargen

[11] Patent Number: 6,069,694
[45] Date of Patent: May 30, 2000

[54] FLOW CELL

[75] Inventor: Kenneth P. VonBargen, Berwyn Heights, Md.

[73] Assignee: Foss NIRSystems, Inc., Silver Spring, Md.

[21] Appl. No.: 09/087,144

[22] Filed: May 29, 1998

[51] Int. Cl.[7] .................................................. G01N 1/10
[52] U.S. Cl. ........................................................... 356/246
[58] Field of Search .................................. 356/244, 246; 250/227.11, 227.24; 385/90, 25, 26, 27, 52

[56] References Cited

U.S. PATENT DOCUMENTS

| | | | |
|---|---|---|---|
| 4,988,155 | 1/1991 | Harner et al. .......................... | 350/96.1 |
| 5,168,367 | 12/1992 | O'Rourke et al. ...................... | 356/246 |
| 5,268,736 | 12/1993 | Prather .................................... | 356/246 |
| 5,302,272 | 4/1994 | Klein ...................................... | 204/299 R |
| 5,442,437 | 8/1995 | Davidson ................................ | 356/246 |
| 5,452,082 | 9/1995 | Sanger et al. .......................... | 356/246 |
| 5,521,384 | 5/1996 | Lynch ..................................... | 250/343 |

*Primary Examiner*—Frank G. Font
*Assistant Examiner*—Michael P. Stafira
*Attorney, Agent, or Firm*—Lane, Aitken & McCann

[57] ABSTRACT

In a flow cell, a flow cell body defines a fluid passageway. Opposed fiber optic cable assemblies with sapphire windows project into the fluid passageway. The fiber optic cable assemblies are axially adjustable in position to provide a capability of varying the path length for the light beam passing between the sapphire windows of the fiber optic cable assemblies in the fluid flowing in the fluid flow path. The path length is precisely settable by means of a feeler gauge which is inserted in a position between the windows of the fiber optic cable assemblies by means of a fixture inserted into the flow path. The fixture is in two parts which engage the fiber optic cable assemblies from opposite ends of the flow path and the fixture is provided with an oblong slot to properly orient the feeler gauge in the flow path between the fiber optic cable assemblies.

11 Claims, 4 Drawing Sheets

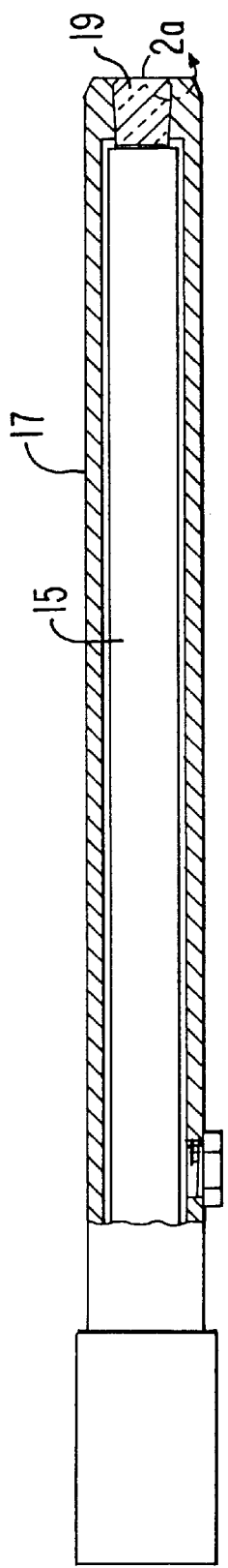
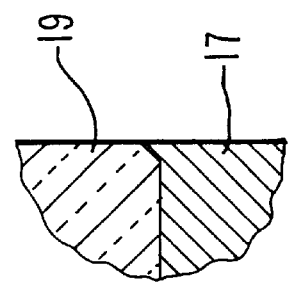
FIG. 2
FIG. 2a

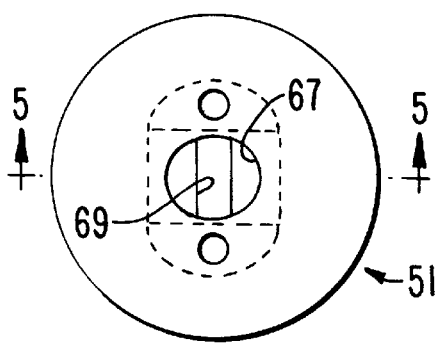
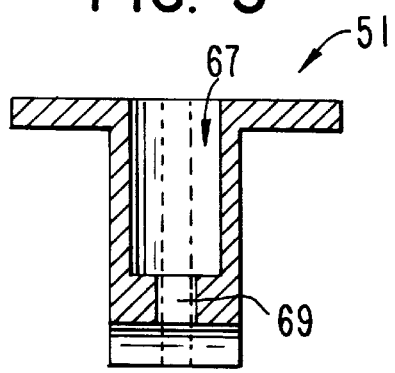
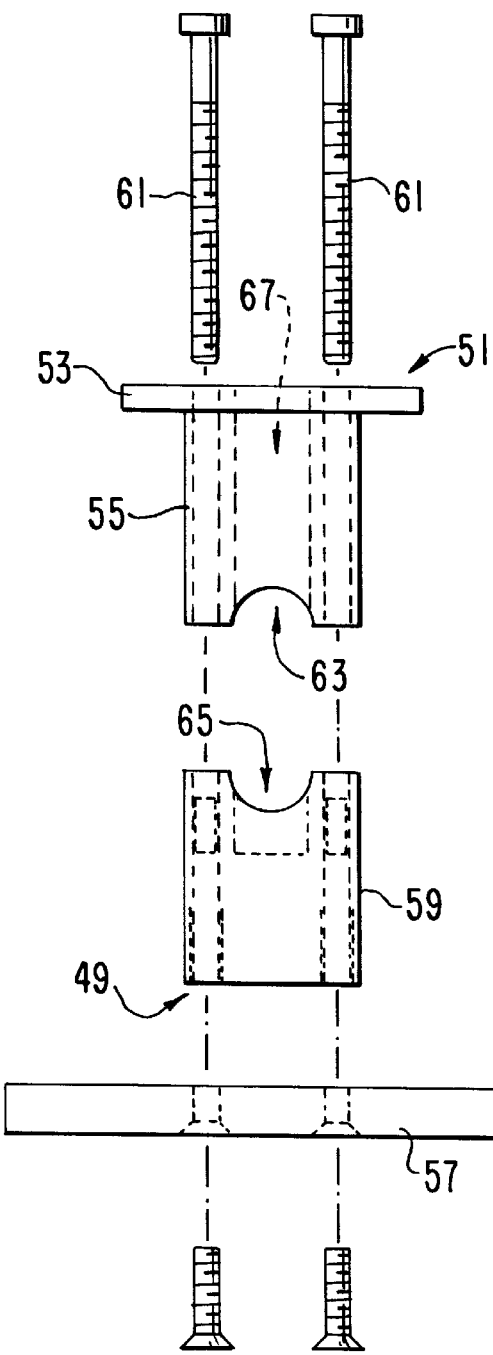

FLOW CELL

BACKGROUND OF THE INVENTION

This invention relates to an improved flow cell for an optical measuring system. The invention is particularly suited for use in connection with the infrared measurement of liquid dairy products and other liquid food products.

Optical sensing is a common non-invasive manner to measure the various constituents which make-up food products. One effective technique of optical sensing is performed using an infrared light source, fiber optic cables and photodetectors. Infrared light is passed through a food sample and light transmitted through the sample is measured and analyzed by photodetectors. The data generated by the photodetectors can provide an accurate measurement of a given sample's constituent make-up because each component has unique absorbance properties and thus a unique optical signature in the infrared range.

One application for this technology involves optical sensing in connection with the production and processing of dairy products. In the production of dairy products it is desirable to quantitatively measure various constituents of the product such as fat, water, solids and sugar content from a stream of flowing liquid. Measurement of these components involves passing the flowing liquid stream through a light beam emitted from an infrared source and then measuring the light transmitted through the sample with photodetectors. The apparatus which provides a facility to direct an infrared light beam through a flowing sample stream is referred to as a flow cell. Light generated from an infrared source is transmitted through a fiber optic cable to a window in the flow cell which is transparent to infrared light. Infrared light passes through the window and then through the sample stream passing through the flow cell. Light that is not absorbed by the sample then passes through an opposite window to be received by a second fiber optic cable. The second cable transmits the incident light to a photodetector where the intensity of the transmitted light is measured. The various constituents of food products such as milk, salad dressing, cheese, and yogurt have unique absorbance spectra in the infrared range. Quantitative measurements of the constituents of the food products can be by carried out measuring the light transmitted through the sample at predetermined wavelengths in the near infrared range. Using a device as described herein, a food producer can continuously monitor the various levels of constituents in his product throughout the production phase.

In prior art systems, fiber optic cables transmitting infrared light are received in a flow cell by opposite cylindrical extensions positioned perpendicular to an axis parallel to the direction of flow of the sample. Fiber optic cables are received in cavities of closed ended tubes which define distal circular window areas. In the prior art flow cells, the closed ended tubes are made of polysulphone. The tubes radially extend from the sidewalls of the flow cell and into the conduit carrying the food product to position the windows opposite one another. The windows are positioned in this manner so that light only passes through a reduced sample section as compared to the diameter of the conduit. Such a reduced section is generally required because an adequate amount of infrared light cannot sufficiently penetrate a long distance through a sample to enable a photodetector to make accurate measurements. The optimal distance between the opposite windows in a flow cell is dependent on the product that will be measured.

Standard operating practice in the dairy industry dictates that the conduits carrying food products and all the fittings used therein be thoroughly cleaned on a daily basis. Because flow cells are within the conduits and are in contact with the food products they must also be disassembled and cleaned after each use. Generally accepted design parameters for conduits designed to carry dairy products attempt to keep the interior surface of the conduits as smooth and even as possible. Any interruption of the interior surface, such as a crevice, provides a harbor for food products to accumulate, coagulate and spoil. The presence of coagulated milk or dairy products within a conduit provides a suitable environment for the growth of harmful bacteria which can contaminate food product passing through a particular conduit. Moreover, an accumulation can be abruptly released into the food product further contaminating the supply.

The use of closed ended tubes to receive the fiber optic cables were effective in eliminating any crevices or gaps exposed to the flow path at the distal ends of the polysulfone tubes because these tubes were molded of one piece. However, the closed ended tube structure meant that the infrared light had to be passed through polysulfone windows at the distal end of tubes and while polysulfone is transmissive of infrared light, it nevertheless provides significant attenuation of the near infrared light. In addition, the polysulfone is susceptible to cracking when subjected to the high pressure that occurs in the fluid in the flow cell.

In a flow cell, it is sometimes necessary or desirable to adjust the path length in the material through which the infrared light travels to account for liquids with different degrees of absorption. In a prior art flow cell, this adjustment was carried out by changing the length of the closed ended tubes which housed the fiber optic cables and a path length adjustment required a partial disassembly of the flow cell to change to a different length closed ended polysulfone tube.

SUMMARY OF THE INVENTION

The present invention improves over the prior art flow cells by providing a flow cell in which the fiber optic cables are housed in stainless steel tubes which project into the flow cell and which have at their distal ends sapphire windows. The sapphire windows and tubes are constructed so that no crevice or gap is found at the joint between the windows and the stainless steel tubular casings housing the fiber optic cables and the windows. The positions of the stainless steel tubes in the flow cell are axially adjustable so that the distance between the sapphire windows at the distal ends of the stainless steel tubes are adjustable, thus providing adjustment of the path length of the infrared light beam in the fluid flowing between the sapphire windows. The fluid in the flow cell is typically at a high pressure which will tend to force the fiber optic cable assemblies back out of the flow cell. Clamps strongly, but releasably, holding the stainless steel tubes in position are provided to prevent the pressure from pushing the filter optic cable assemblies back out of the flow cell while at the same time enabling the axial position of the fiber optic cable assemblies to be adjusted.

In the analysis of the fluid flowing in the flow cell, the path length of the infrared light beam in the fluid must be precisely known and, accordingly, it is necessary to be able to precisely set the path length between the sapphire windows within the flow cell. To carry out this path length setting, a fixture is provided which can be mounted on the flow cell. The fixture positions a feeler gauge centered in the flow cell. With the feeler gauge in position, the coaxial cable assemblies are moved axially inward to engage the feeler gauge and then the optical cable assemblies are clamped in a fixed axial position. In this manner, the path length that the infrared light travels through the fluid being analyzed can be adjusted and precisely set at a predetermined known path length.

BRIEF DESCRIPTION OF THE DRAWINGS

FIG. 2 is a sectional view of fiber optic cable assembly used in the flow cell of FIG. 1;

FIG. 2a is an enlarged sectional view of the portion of FIG. 2 within the circle 2a;

FIG. 3b is an exploded view of the clamp shown in FIG. 3a;

FIG. 4 is an exploded view of the fixture used in the flow cell to precisely determine the spacing between the distal ends of the fiber optic cable assemblies in the flow cell;

FIG. 5 is an axial sectional view in elevation of the upper component of the fixture shown in FIG. 4 taken along the line 5—5; and FIG. 6 is a top plan view of the component shown in FIG. 5.

DESCRIPTION OF A PREFERRED EMBODIMENT

Figure 1:
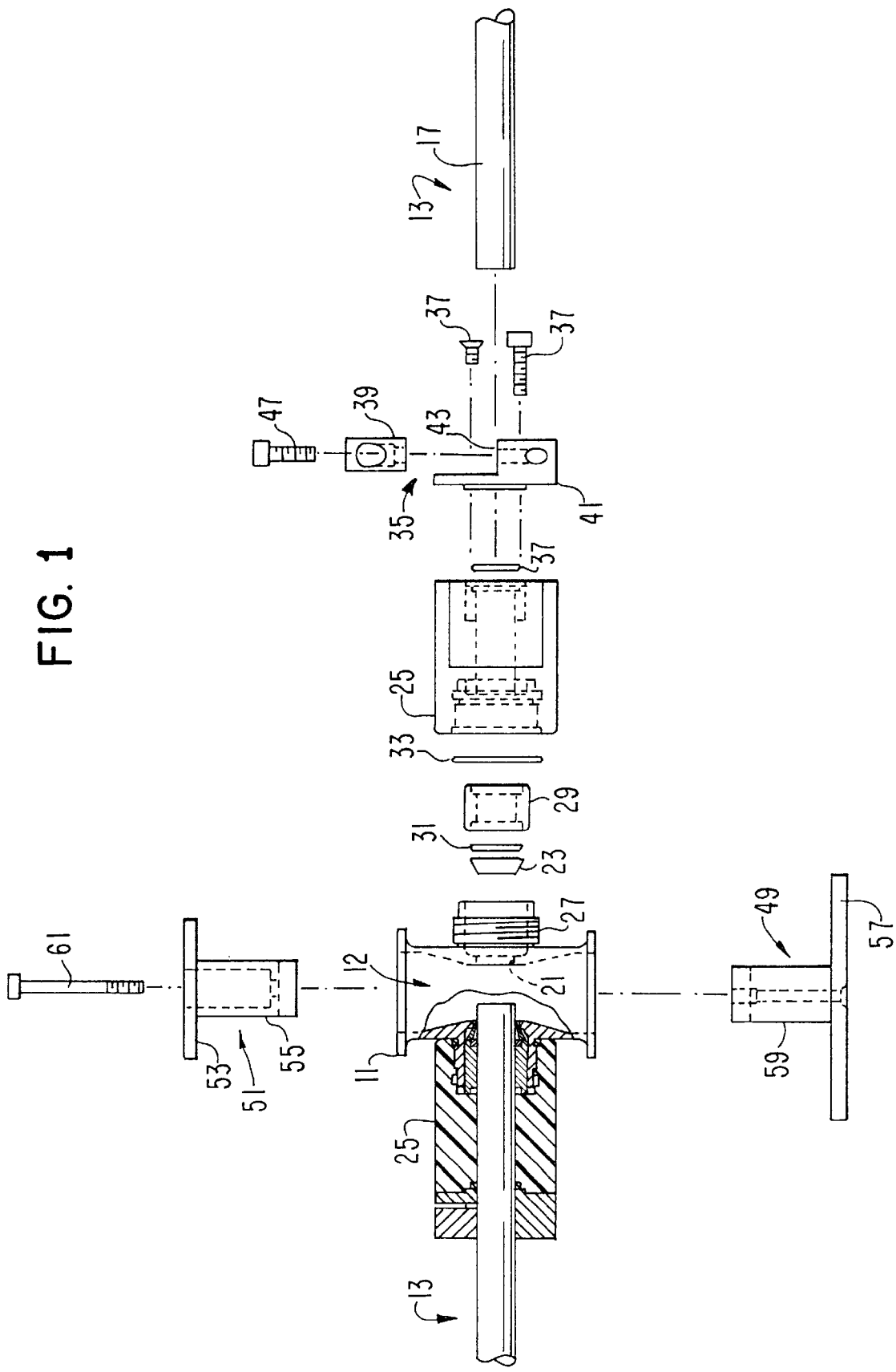
FIG. 1 is a partial exploded and partial sectional view of the flow cell of the present invention.

The flow cell of the invention as show in FIG. 1 comprises a flow cell body 11 defining a generally cylindrical vertical passageway for fluid to be analyzed by infrared analysis. The fiber optic cable assemblies 13 extend from opposite sides of the flow cell into the cylindrical passageway 12 and are spaced apart a predetermined distance from each other in the flow cell to define a precisely determined path length between the distal ends of the fiber optic cable assemblies 13 for infrared light to travel through the flowing stream of the fluid to be analyzed.

As shown in FIG. 2, each fiber optic cable assembly comprises a fiber optic cable 15 enclosed in a stainless steel tubular cylindrical casing 17. The distal end of the fiber optic cable 15 abuts against a planar inner surface of a sapphire window 19. The sapphire window 19 fits in a tapered aperture formed in the distal end of the casing 17. The sapphire window 19 is frustoconical in shape to fit with the tapered shape of the aperture and the circular edge at the boundary of the outer surface of the window 19 is chamferred. The stainless steel material of the casing 17 is cold flowed into the small crevice formed by the chamferred edge of the window 19 so that a perfectly flat surface is presented at the distal end of the fiber optic cable assembly with no discernable crevices. Infrared light from an infrared analyzing instrument is introduced at the proximal end of one of the fiber optic cables 13 and travels through this fiber optic cable 15 and then through the corresponding sapphire window to be transmitted through the fluid flowing between the distal ends of the fiber optic assemblies in the flow path 12. The infrared light then is transmitted through the sapphire window of the receiving fiber optic cable assembly and then through the fiber optic cable of the receiving assembly to the infrared analysis instrument. The light introduced into the fiber optic cable 15 may be a narrow bandwidth of infrared light which is scanned through the infrared spectrum by an optical grating so that the light traveling through the fluid is narrow bandwidth light scanned through the infrared spectrum. Alternatively, the light after passing through the fluid sample to be analyzed may be scanned by an optical grating through the infrared spectrum.

The fiber optic assemblies 13 each extend into the passageway 12 through identical mounting structures. Each assembly 13 passes through an aperture 21 in the sidewall of the cell body 11. A Teflon ferrule 23, having a cylindrical inner wall fitting with the outer cylindrical wall of the casing 17 and having a tapered outer surface, is pressed between the casing 17 and a correspondingly tapered wall of the aperture 21 to minimize the presence of any crevices at the joint between the casing 17 and the wall of the cell body 11 defining the passageway 12. The ferrule 23 is forced into the space between the casing 17 and the wall of the opening 21 by a Teflon nut 25 which is screwed onto an extension 27 surrounding the opening 21. The nut 25 makes a sliding fit with the casing 17 and has an opening at its inner end to engage a stainless steel spacer 29, which in turn engages a back Teflon ferrule 31. The back ferrule 31 engages the back side of the ferrule 23. As the nut 25 is screwed onto the extension 35, it applies axial force to the spacer 29 which in turn applies a force to the back ferrule 31. The back ferrule 31 in turn forces the ferrule 23 into the annular space between the wall of the aperture 21 and the outer wall of the casing of the assembly 13. An O-ring 33 is provided on a non-threaded end portion of extension 27 and is received in an O-ring channel within the opening at the inner end of the nut 25 to prevent entry of moisture into the volume surrounding the assembly 13 within the nut 25 and the extension 27.

A clamp 35 releasably engages the casing 17 and holds it with sufficient force to prevent the fluid pressure within the channel 12 from forcing the assembly 13 back out of the channel 12. An O-ring 37 is provided in an O-ring channel on the back end of the nut 25 in sealing engagement with the surface of the casing 17 to prevent entry of moisture into the volume around the assembly 13 within the nut 25.

Figure 3A:
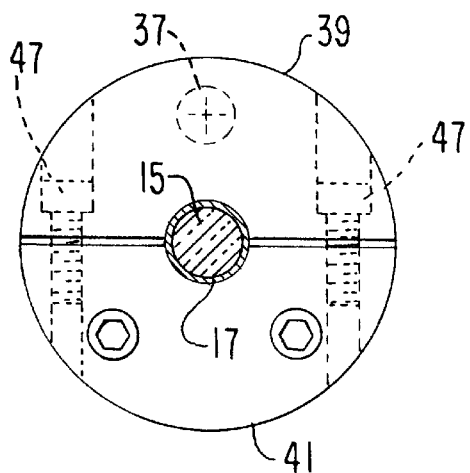
FIG. 3a is a sectional view showing an elevational view of a clamp used to hold a fiber optic assembly in position in the flow cell.
Figure 3B:
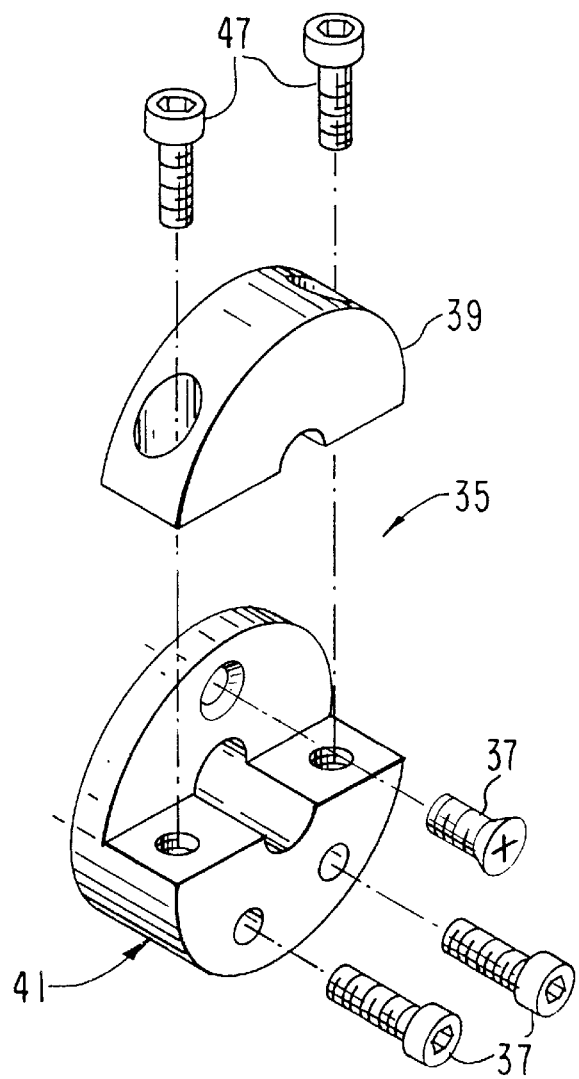

As shown in FIGS. 3a and 3b, the clamp 35 comprises upper clamping member 39 and a lower clamping member 41, each formed with a cylindrical slot to engage and clamp on the outer cylindrical surface of the assembly 13. The cylindrical slots in the clamping members are less than half cylinders so that when the clamping members engage the assembly 13, they can be pressed together to apply substantial force to the assembly 13 and hold the assembly 13 in position. The lower clamping member 41 has an inner face plate which is mounted on the outer end of the nut 25 by means of screws 38. The lower clamping member 41 has a circular perimeter and has a 180 degree sector cut out of the outer end of the member 41 leaving a flat surface 43 located on the axis of the clamping member 41. One of the two cylindrical slots for engaging the casing 17 is formed in the planar surface 43. The upper clamping member 39 is D-shaped and fits in the cut-out sector of the outer side of the lower clamping member 41. The lower surface of the clamping member 39 is planar and is positioned opposite the planar surface 43. Screws 47 extend through bores in the upper clamping member 39 and are threaded into holes in the lower clamping member 41 and by means of the screws 47, the clamping members are brought together to clamp on the cylindrical surface of the casing 17 to hold the fiber optic cable assembly in axial position.

The flow cell has a fixture having an lower part 49 and an upper part 51 for precisely setting the gap between the distal ends of the fiber optic cable assemblies 13 and the passageway 12. The upper fixture part 51 has a top flange 53 which can rest on the top of the flow cell body 11 and a cylindrical portion 55 which extends down into the passageway 12. The lower fixture part 49 has a lower flange 57 which can engage the lower surface of the flow cell body 11 rests. A cylindrical portion 59 of the lower fixture part 49 extends into the passageway 12 from the lower end thereof. The parts of the fixture are held together in the passageway 12 by screws 61.

As better shown in FIGS. 4–6, the lower surface of the upper part 51 of the fixture has a cylindrical slot 63 defined therein for engaging the fiber optic cable assemblies 53 when the fixture is assembled in the passageway 12. Similarly, the lower fixture member 49 has a cylindrical slot 65 which engages the fiber optic cable assemblies when the fixture is assembled in passageway 12. The upper part 51 has a cylindrical bore 67 which extends from the top of the upper member 51 to an oblong slot 69 which is positioned to orient the plate of the feeler gauge, which is inserted through the opening 67 and through the slot 69 to be perpendicular to the axes of the fiber optic cable assemblies 13. The lower end of the feeler gauge is received in recess 71 defined in the upper end of the lower fixture part 49.

The feeler gauge is a flat piece of metal having a thickness corresponding to the desired path length for the flowing liquid sample. When the feeler gauge is inserted in the fixture, it will be in position between the coaxial cable assemblies 13. With the clamps 35 loosened, the coaxial cable assemblies 13 are slid inwardly to engage opposite sides of the feeler gauge and the clamps 35 are then tightened to firmly hold the coaxial cable assemblies 13 in position whereupon the feeler gauge and the upper and lower parts 49 and 51 of the feeler gauge fixture are removed leaving the path length between the windows 19 of the fiber optic cable assemblies precisely set at the desired dimension. The clamps 35 must be tightened against the cable assemblies 13 with sufficient force to prevent the pressure that will come to exist in the passageway 12 from being able to axially push the cable assemblies back out of the flow channel 12.

With the system as described above, a flow cell is provided with sapphire windows between the fiber optic cables and the fluid passageway and in which the axial position of the fiber optical cables can be adjusted. By means of the feeler gauge fixture and feeler gauges, the gap between the distal ends of the fiber optic cable assemblies can be precisely set to a desired path length for the infrared radiation to travel through the liquid sample.

The above description is of a preferred embodiment of the invention and modifications may be made thereto without departing from the spirit and scope of the invention, which is defined in the appended claims.

I claim:

1. A flow cell for optically analyzing fluids comprising a cell body defining a fluid passageway, first and second opposed fiber optic cable assemblies extending through the walls of said cell body projecting into said fluid passageway, said assemblies comprising tubular metal casings housing fiber optic cables and each having a sapphire window at the distal end thereof in said fluid passageway, the sapphire windows of said fiber optic cable assemblies defining a path length for light transmitted through said fiber optic cable assembles to be transmitted through fluid flowing in the gap between said opposed cable assemblies, and clamps releasably engaging said tubular metal casings to hold said cable assemblies in fixed axial positions by frictional force between said clamps and said tubular metal casings when said clamps engage said tubular metal casings and to permit said cable assemblies to slide axially when said clamps are released from said tubular metal casings so that the axial positions of said fiber optic cable assemblies can be adjusted to thereby permit said path length to be adjusted, said clamps each comprising first and second clamping members arranged to engage opposite sides of the tubular metal casing of a cable assembly, said clamping members defining cylindrical slots shaped to fit with said tubular metal casing, said slots being less than half cylinders, said clamps having means to force said clamping members together to frictionally engage said tubular metal casings with said cylindrical slots.

2. A flow cell as recited in claim 1, further comprising a fixture removably mountable in said fluid passageway, said fixture comprising means to support a feeler gauge in said passageway between the ends of said fiber optic cable assemblies.

3. A flow cell as recited in claim 2, wherein said fixture comprises first and second parts having slots shaped to engage said fiber optic cable assemblies from the upstream and downstream ends of said flow path and means to couple said first and second parts of said fixture together in said flow path and in engagement with said fiber optic cable assemblies.

4. A flow cell as recited in claim 2, wherein said fixture defines an oblong slot to receive a feeler gauge and orient a metal plate of said feeler gauge generally perpendicular to the axes of said fiber optic cable assemblies.

5. A flow cell comprising a flow cell body defining a fluid passageway, opposed fiber optic cable assembles extending through the walls of said fluid cell and projecting into said fluid passageway and clamps for releasably engaging said fiber optic cable assemblies to hold said cable assemblies in fixed axial positions by frictional force between said clamps and said cable assemblies when said clamps engage said cable assemblies and to permit said cable assemblies to slide axially when said clamps are released from said cable assemblies so that the axial positions of said fiber optic cable assemblies can be adjusted to thereby permit the spacing between the ends of said fiber optic cable assemblies to be adjusted, a fixture removably mounted in said fluid passageway, said fixture comprising means to support a feeler gauge in said passageway between the ends of said fiber optic cable assemblies.

6. A flow cell as recited in claim 5, wherein said fixture comprises first and second parts having slots shaped to engage said fiber optic cable assemblies from the upstream and downstream ends of said flow path and means to couple said first and second parts of said fixture together in said flow path and in engagement with said fiber optic assemblies.

7. A flow cell as recited in claim 5, wherein said fixture defines an oblong slot to receive a feeler gauge and orient a metal plate of said feeler gauge generally perpendicular to the axes of said fiber optic cable assemblies.

8. A method of setting a path length between opposed windows in the distal ends of fiber optic cable assemblies in a flow cell comprising selecting a feeler gauge having a width corresponding to the desired path length and inserting said feeler gauge into said passageway, axially moving said fiber optic cable assemblies to engage said feeler gauge and then engaging said fiber optic cable assemblies with clamps to hold said fiber optic cable assemblies in their axial positions with frictional force in engagement with said feeler gauge.

9. A method of setting a path length as recited in claim 7, further comprising inserting a fixture into said fluid passageway having an aperture to orient said feeler gauge in the middle of said passageway with the plate of said feeler gauge perpendicular to the axes of said fiber optic cable assemblies.

10. A method of setting a path length as recited in claim 9, wherein said fixture has first and second parts which are inserted into said flow path from the upstream and downstream ends thereof to engage said fiber optic cable assemblies.

11. A method of setting a path length as recited in claim 10, further comprising coupling said first and second parts of said fixture together in engagement with said fiber optic cable assemblies, said gauge being inserted into said fixture between said fiber optic cable assemblies after said first and second parts of said fixture have been coupled together.

* * * * *